(12) United States Patent
Lin et al.

(10) Patent No.: US 6,302,882 B1
(45) Date of Patent: Oct. 16, 2001

(54) TRANSVERSE ROD CONNECTOR CLIP

(75) Inventors: Chih-I Lin, Diamond Bar, CA (US); David Nichols, Memphis, TN (US)

(73) Assignee: Surgical Dynamics, Inc., Norwalk, CT (US)

(*) Notice: Subject to any disclaimer, the term of this patent is extended or adjusted under 35 U.S.C. 154(b) by 0 days.

(21) Appl. No.: 09/578,637

(22) Filed: May 25, 2000

Related U.S. Application Data

(62) Division of application No. 08/856,916, filed on May 15, 1997, now abandoned.

(51) Int. Cl.[7] .................................................. A61B 17/70
(52) U.S. Cl. .................................................. 606/61
(58) Field of Search ................................. 606/60, 61, 72, 606/73, 53, 54

(56) References Cited

U.S. PATENT DOCUMENTS

| | | |
|---|---|---|
| 2,439,995 | 4/1948 | Thrailkill . |
| 4,269,178 | 5/1981 | Keene . |
| 4,611,582 | 9/1986 | Duff . |
| 4,641,636 | 2/1987 | Cotrel . |
| 4,815,453 | 3/1989 | Cotrel . |
| 4,887,596 | 12/1989 | Sherman . |
| 5,010,879 | 4/1991 | Moriya et al. . |
| 5,074,864 | 12/1991 | Cozad et al. . |
| 5,084,049 | 1/1992 | Asher et al. . |
| 5,108,397 | 4/1992 | White . |
| 5,112,332 | 5/1992 | Cozad et al. . |
| 5,116,334 | 5/1992 | Cozad et al. . |
| 5,176,679 | 1/1993 | Lin . |
| 5,196,014 | 3/1993 | Lin . |
| 5,257,993 | 11/1993 | Asher et al. . |
| 5,257,994 | 11/1993 | Lin . |
| 5,275,600 | 1/1994 | Allard et al. . |
| 5,281,222 | 1/1994 | Allard et al. . |
| 5,304,179 | 4/1994 | Wagner . |
| 5,330,473 | 7/1994 | Howland . |
| 5,330,474 | 7/1994 | Lin . |
| 5,334,203 | 8/1994 | Wagner . |
| 5,346,493 | 9/1994 | Stahurski et al. . |
| 5,368,594 | 11/1994 | Martin et al. . |
| 5,380,326 | 1/1995 | Lin . |
| 5,437,671 | 8/1995 | Lozier et al. . |
| 5,439,463 | 8/1995 | Lin . |

(List continued on next page.)

FOREIGN PATENT DOCUMENTS

| | | |
|---|---|---|
| 2215485 | 9/1996 | (CA) . |
| 2206853 | 12/1997 | (CA) . |
| 0553042A1 | 1/1993 | (EP) . |
| 0 565 149 A2 | 10/1993 | (EP) . |
| 0811357 | 8/1997 | (EP) . |
| 2730155 A | 7/1993 | (FR) . |
| 2051581 | 6/1980 | (GB) . |

Primary Examiner—David O. Reip

(57) ABSTRACT

A transverse connector clip for connecting cylindrical rods to each other in a spinal fixation system, comprising a clip body having two sides. The first side of the clip body has a longitudinal axis and a pair of mirror image hemi-cylindrical shells. These hemi-cylindrical shells have an inner diameter that is slightly smaller than the outer diameter of a cylindrical rod. The clip body is shaped so as to allow the hemi-cylindrical shells to spread around the cylindrical rod when the cylindrical rod is inserted between said shells and to securely clamp on the cylindrical rod at a 90° angle relative to the clip body The second side of the clip body can comprise one of several embodiments; a short laterally extending hemi-cylinder rod, a laterally extending hemi-cylinder rod with a plurality of vertical teeth, a second pair of mirror image hemi-cylindrical shells, a laterally extending rod tapering from a proximal cylindrical shape to a distal hemi-cylinder shape, or a body portion and a locking mechanism configured to receive and lock a hemi-cylindrical or cylindrical rod.

13 Claims, 6 Drawing Sheets

U.S. PATENT DOCUMENTS

| | | |
|---|---|---|
| 5,476,462 | 12/1995 | Allard et al. . |
| 5,498,262 | 3/1996 | Bryan . |
| 5,507,746 | 4/1996 | Lin . |
| 5,520,688 | 5/1996 | Lin . |
| 5,527,314 | 6/1996 | Brumfield et al. . |
| 5,562,662 | 10/1996 | Brumfield et al. . |
| 5,562,663 | 10/1996 | Brumfield et al. . |
| 5,591,165 | 1/1997 | Jackson . |
| 5,609,592 | 3/1997 | Brumfield et al. . |
| 5,611,800 | 3/1997 | Davis et al. . |
| 5,613,968 | 3/1997 | Lin . |
| 5,630,816 | 5/1997 | Kambin . |
| 5,630,817 | 5/1997 | Rokegem et al. . |
| 5,752,955 * | 5/1998 | Errico ................................. 606/61 |
| 5,947,966 * | 9/1999 | Drewry et al. ..................... 606/61 |

* cited by examiner

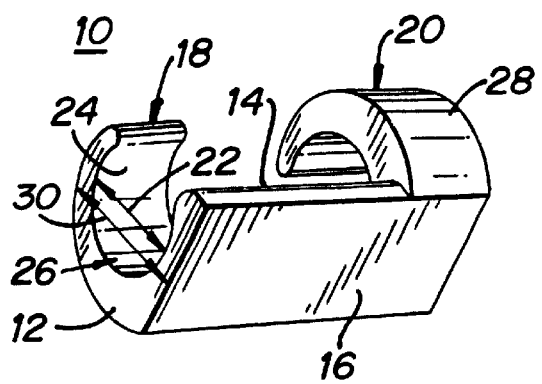
FIG_1
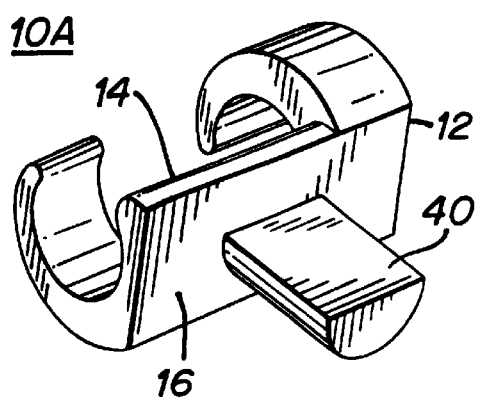
FIG_2
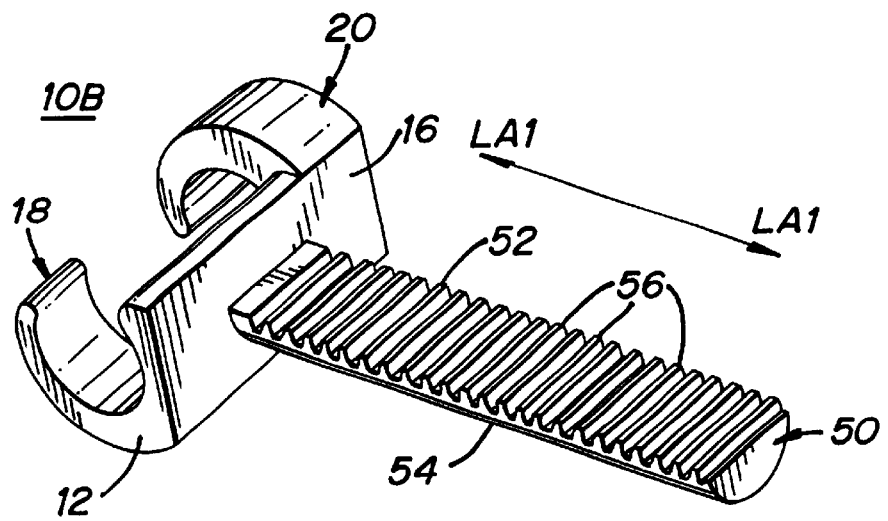
FIG_3
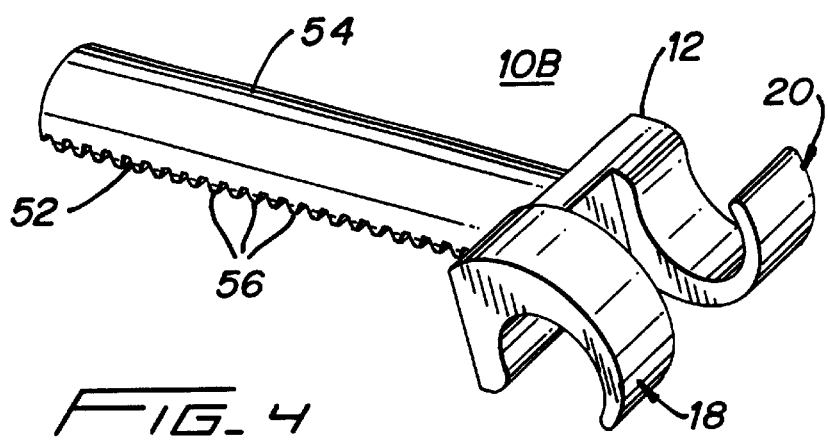
FIG_4

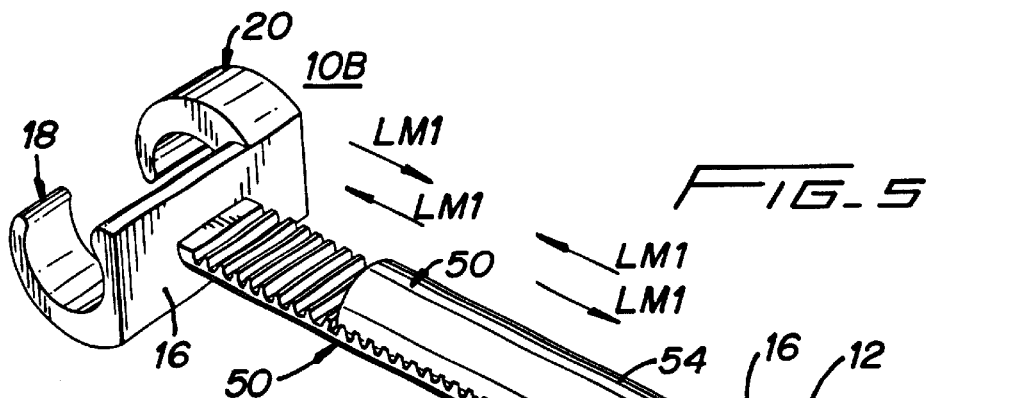
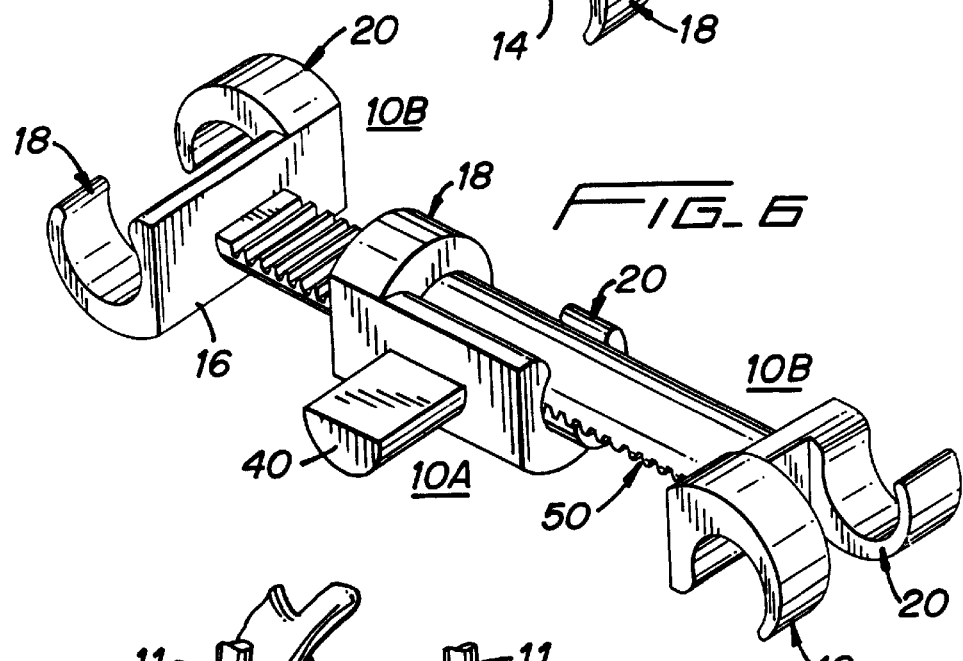
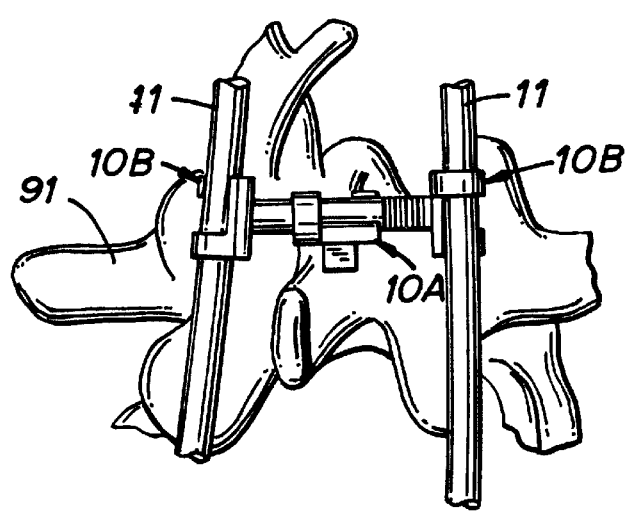

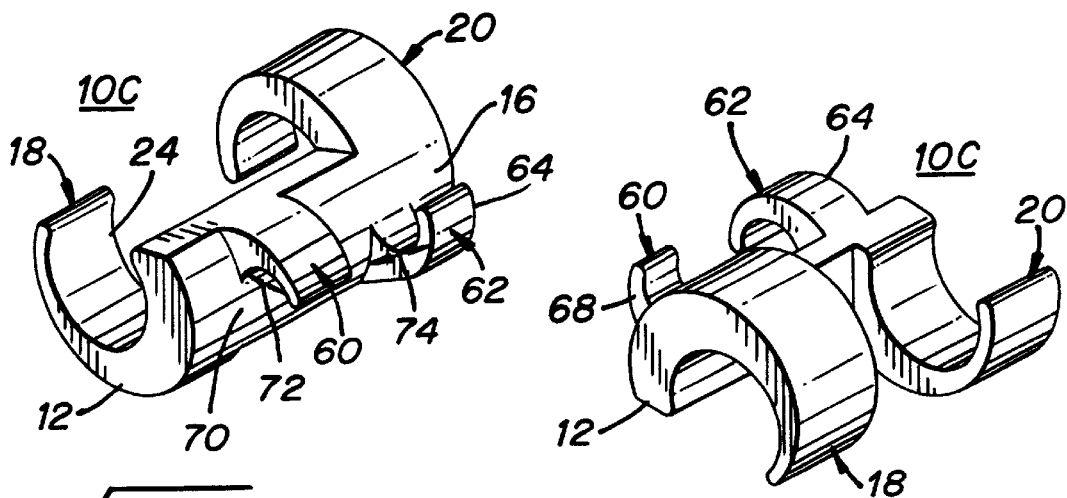
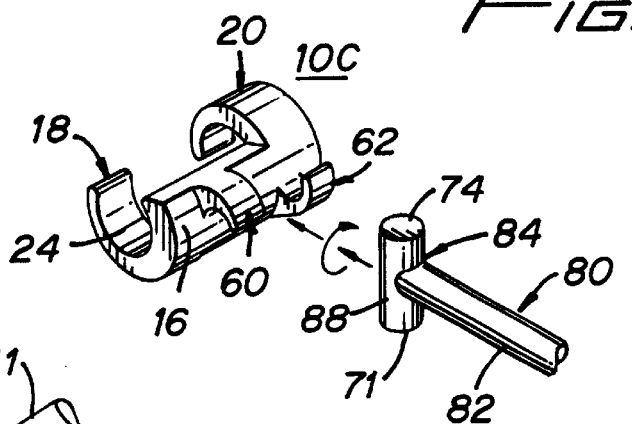
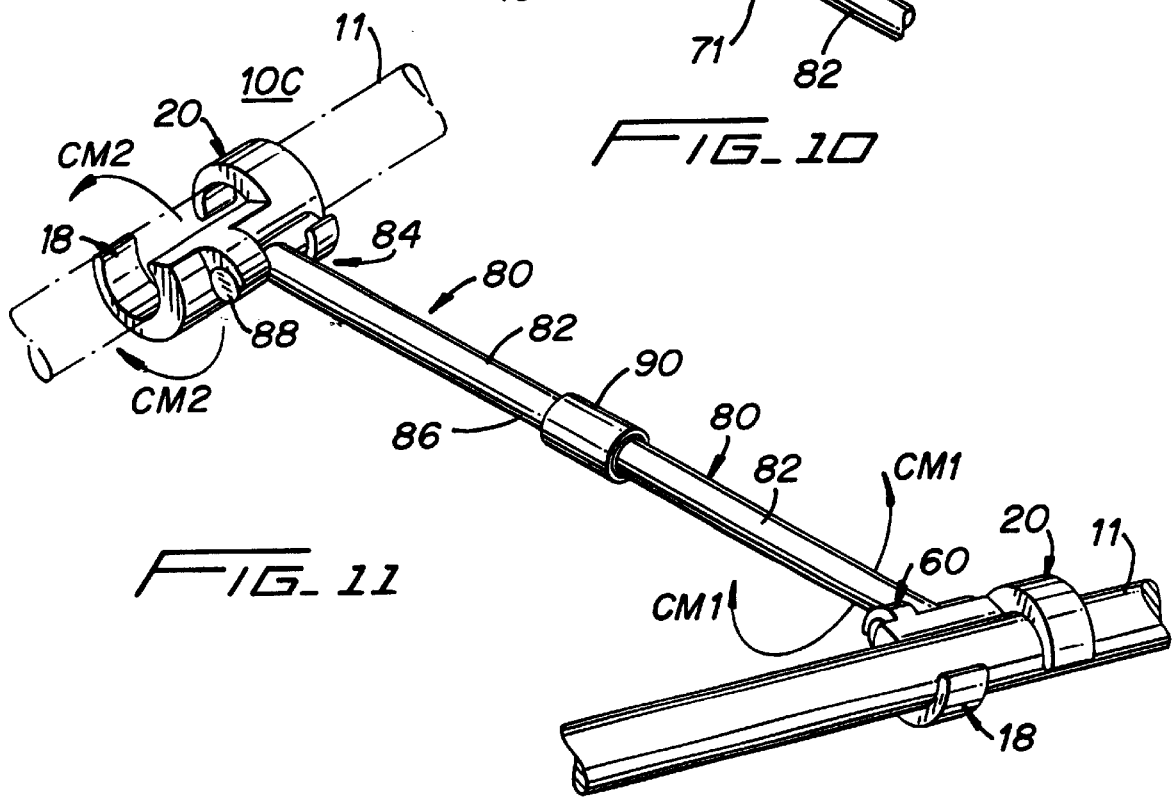

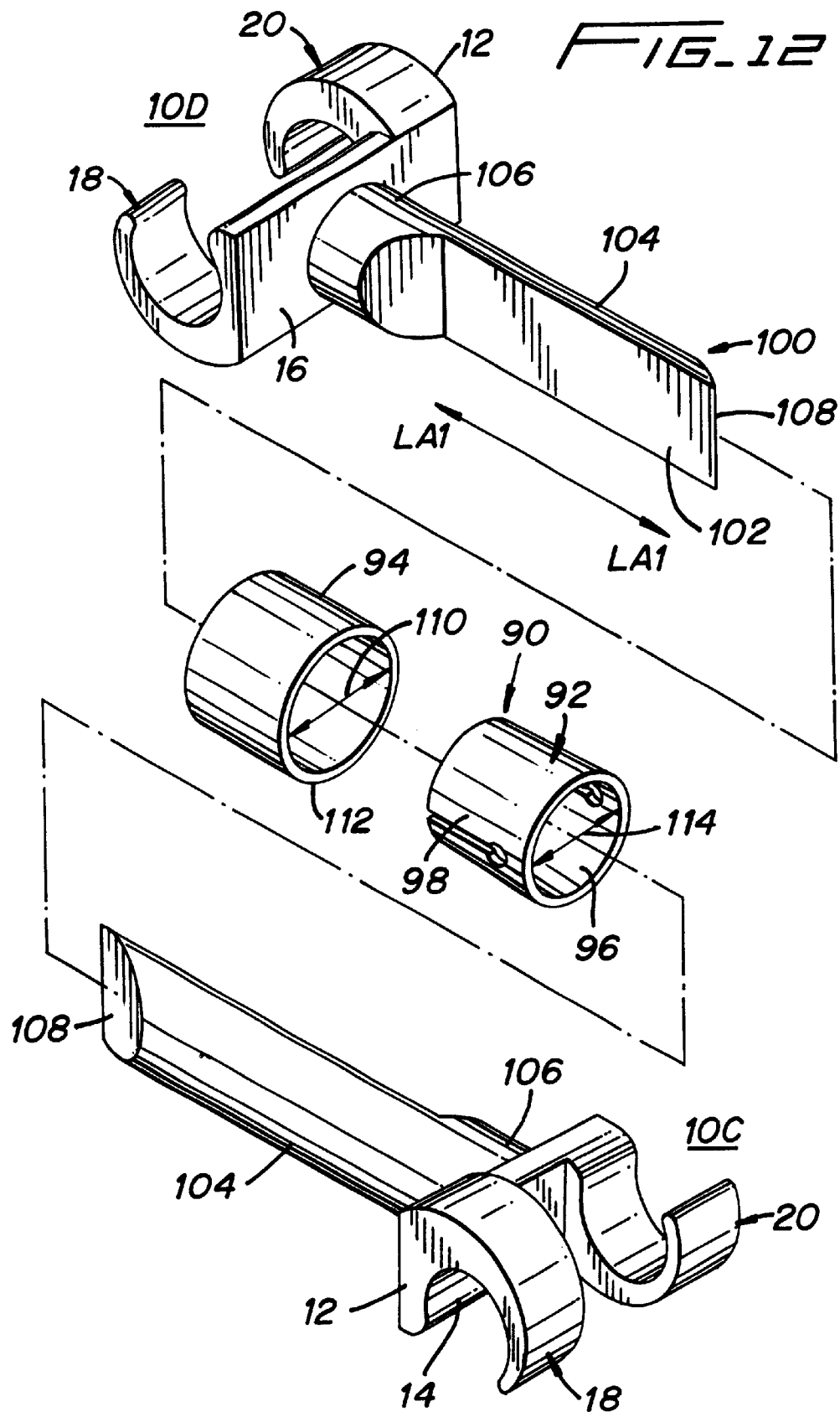

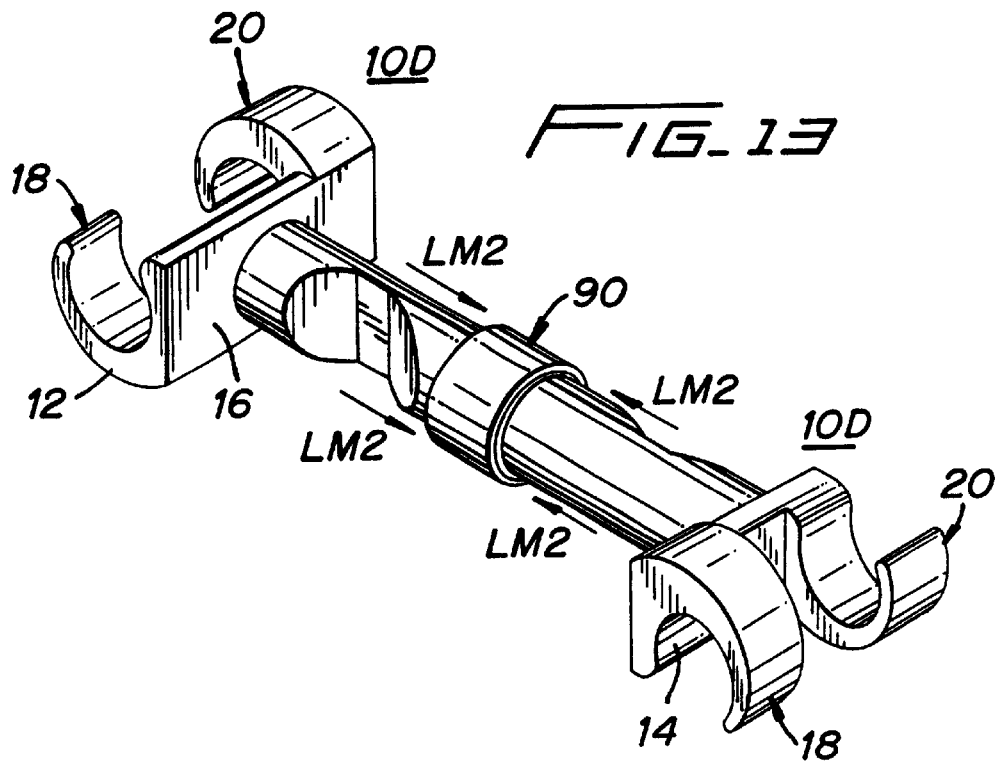
FIG_13
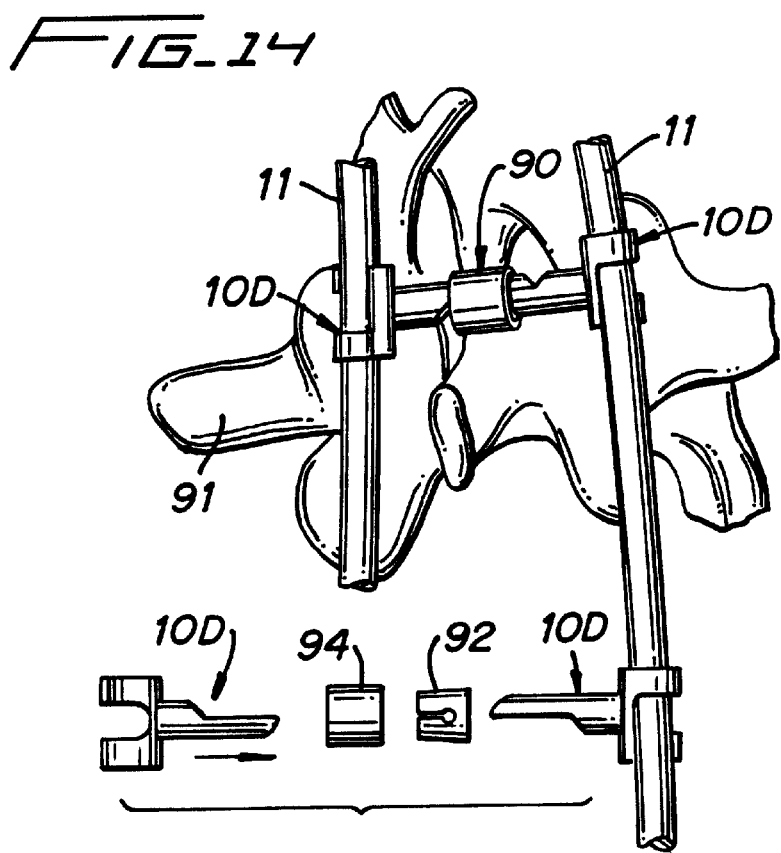
FIG_14

TRANSVERSE ROD CONNECTOR CLIP

This application is a divisional of application Ser. No. 08/856,916, filed May 15, 1997, now abandoned.

BACKGROUND OF THE INVENTION

1. Field of the Invention

The present invention relates to implantable spinal fixation systems for the surgical treatment of spinal disorders. More particularly, this invention relates to a transverse rod connector clip for connecting cylindrical rods to each other.

2. Background of the Invention

For years doctors attempted to restore stability to the spine by fusion (arthrodesis) of the problem area. This treatment yielded marginal results due to the inherently flexible spinal column. Over the past ten years spinal implant systems have been developed to add stability to the spine to enhance the arthrodesis rates. Such systems often include spinal instrumentation having connective structures such as a pair of plates and/or rods which are placed on opposite sides of the portion of the spinal column which is intended to be fused. These spinal systems consist of screws and hooks for segmental attachment to the spine and longitudinal rods connected to screws or hooks. These components provide the necessary stability both in tension and compression yet yield minimal torsional control.

It has been found that when a pair of spinal rods are fastened in parallel on either side of the spinous process, the assembly can be significantly strengthened by using at least one additional rod to horizontally bridge the pair of spinal rods. A cross brace assembly is disclosed in U.S. Pat. No. 5,084,049. Devices such as these commonly consist of a threaded rod for providing the desired lateral support. The threaded rod is fastened to each of the spinal rods by clamps located on each end of the threaded rod. However, this configuration is bulky and can cause irritation of the patient's back muscles and other tissue which might rub against the device. A cross brace assembly that fits closer to the spine, preferably in the same general plane as the vertical spinal rods, would reduce the complications associated with bulkier devices.

Most existing transverse connectors consist of rods, plates, and bars linked to the longitudinal rods by coupling mechanisms with set screws, nuts, or a combination of each. These connectors require several components and instruments to build the constructs. Each additional components or instrument required to assemble the connectors adds to the "fiddle factor" of the surgical technique. Examples of these transverse connectors include Transverse Link Device (DLT) and Crosslink manufactured by Sofamor Danek, Trans-Connector manufactured by Synthes, and Modular Cross Connector and Transverse Rod Connector (TRC) manufactured by AcroMed.

Telescopic rod to rod couplers for use in a spinal implant systems have also been described. Prior to the locking member being engaged, the telescoping sections may be easily slid past their extremes and out of engagement with one another. While this is a convenient method of connecting and disconnecting the coupler sections, it can be inconvenient during surgery if the sections accidentally disengage. U.S. Pat. No. 5,275,600 describes a telescopic rod to rod coupler in which the telescopic rod sections are assembled together using a 180 degree twisting motion. This is designed to minimize the risk of the rod sections accidentally disconnecting during the implant procedure.

Presently available spinal fixation systems frequently require careful alignment of the hardware used to connect the components of the spinal instrumentation with each other. A need has thus arisen for improved rod connectors to transversely connect spinal rods without requiring additional manipulation of the spinal instrumentation and to minimize the use of pedicle screws while at the same time reducing requirements to assemble small pieces of hardware during the surgical procedure.

SUMMARY OF THE INVENTION

The present invention is directed to transverse connector clips for connecting cylindrical rods in spinal fixation systems. The transverse connector clips of the present invention have a clip body with a first side and a second side. The first side of the clip body has a longitudinal axis and a pair of mirror image hemi-cylindrical shells. The hemi-cylindrical shells each have an inner diameter that is slightly smaller than the outer diameter of the cylindrical spinal rod. The clip body is shaped to allow the hemi-cylindrical shells to spread around the cylindrical rod when it is inserted between the hemi-cylindrical shells. The deflection of the hemi-cylindrical shells and the inner shell diameter allow the clip body to securely clamp on the cylindrical spinal rod, placing the inserted cylindrical rod at a 90° angle relative to the longitudinal axis of the clip body The transverse connector clips of the present invention can be used to transversely connected spinal rods without requiring additional manipulation of the spinal instrumentation. Because the clips of the present invention do not require any additional locking mechanism, they reduce the assembly of small pieces of hardware during the surgical procedure.

BRIEF DESCRIPTION OF THE DRAWINGS

FIG. 1 is a top perspective view of one embodiment of a transverse connector clip of the present invention;

FIG. 2 is a perspective view of one embodiment of the transverse connector clip of the present invention with a short, laterally extending bar;

FIG. 3 is a top perspective view of another embodiment of a transverse connector clip of the present invention with a laterally extending bar having a plurality of vertical teeth;

FIG. 4 is a bottom perspective view of the invention clip of FIG. 3;

FIG. 5 is a perspective view of a pair of the connecting transverse connector clips of FIG. 3;

FIG. 6 is a perspective view of the clip of FIG. 2 securing the transverse connector clips of FIG. 5;

FIG. 7 is a schematic view of the present invention connected to spinal rods implanted in a human spine and illustrating the method of assembly;

FIG. 8 is a top perspective view an another embodiment of the present invention;

FIG. 9 is a bottom perspective view of the invention of FIG. 8;

FIG. 10 is perspective view of the invention of FIG. 8 illustrating the connecting mechanism of the connector clip;

FIG. 11 is a perspective view of the invention of FIG. 8 connected to the ends of an T-bar;

FIG. 12 is a perspective view of an another embodiment of the present invention illustrating the method of assembly of two connector clips having laterally extending tapered bars connected together with a tapered sleeve;

FIG. 13 is a perspective view of the invention of FIG. 12 illustrating a range of lateral adjustment between the two clips;

FIG. 14 is a schematic view of the invention of FIG. 13 connected to spinal rods implanted in a human spine and illustrating the method of assembly;

DETAILED DESCRIPTION OF INVENTION

Figure 15:
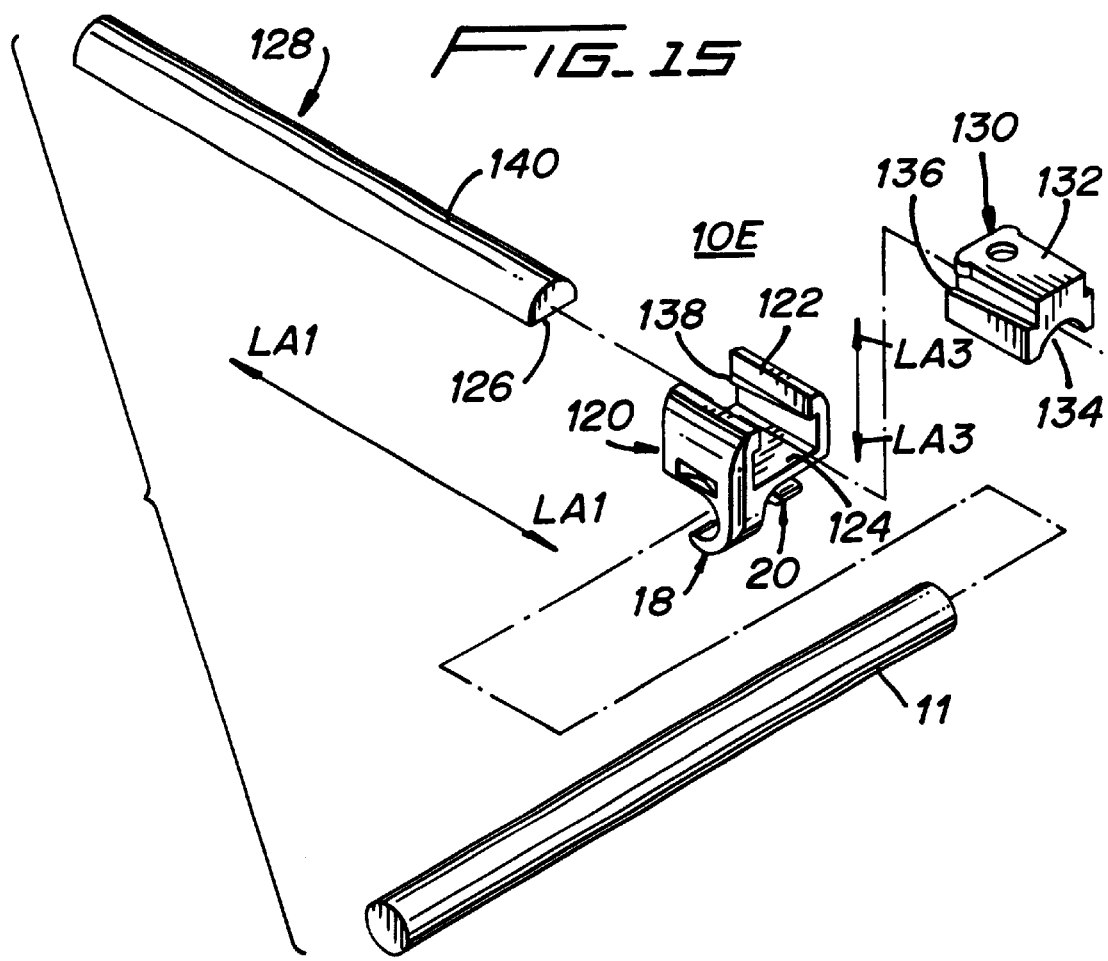
FIG. 15 is a perspective view of another embodiment of the present invention illustrating the method of assembly.

The present invention is directed to a transverse connector clip 10 and assemblies used in spinal fixation systems. Spinal fixation systems typically include spinal instrumentation having connective structures such as a pair of plates and/or rods which are placed on opposite sides of the spinal column near vertebrae that are intended to be fused. These spinal systems consist of screws and hooks for segmental attachment to the spine and longitudinal rods connected to screws or hooks. These components provide the necessary stability both in tension and compression yet yield minimal torsional control. In addition, it has been found that when a pair of spinal rods are fastened in parallel on either side of the spinous process, the assembly can be significantly strengthened by using at least one additional rod to horizontally bridge the pair of spinal rods.

The transverse connector clips 10 of the present invention consist of a component with a means to clip the device on a spinal or cylindrical rod 11 and a component with a means to link two rod connectors together laterally. Transverse connector clip 10 concept consists of a clip body 12 with a first side 14 and a second side 16 (FIG. 1). On first side 14 are two, mirror image hemi-cylindrical shells 18 and 20. These two, mirror image hemi-cylindrical shells 18 and 20 have an inner surface 24 that defines a rod bore 26 through which the cylindrical rod 11 can extend. Rod bore 26 has an inner diameter 22 that is designed to be slightly smaller than the outer diameter of the cylindrical rod 11 it will receive. Top surface 28 of the hemi-cylindrical shells 18 and 20 defines an outer diameter 30.

It should be noted that the two, mirror image hemi-cylindrical shells 18 and 20 can be connected to the first side 14 of clip body 12 as shown in clip 10 A of FIG. 2 or in mirror image relationship as shown in clip 10A of FIG. 6.

Clip body 12 is placed on the cylindrical rod 11 at 90 degrees and turned so that the hemi-cylindrical shells 18 and 20 spread around the rod 11. The deflection of the hemi-cylindrical shells 18 and 20 and the inner diameter of the shells 22 allow the clip 10 to securely clamp on the rod 11.

Figure 16:
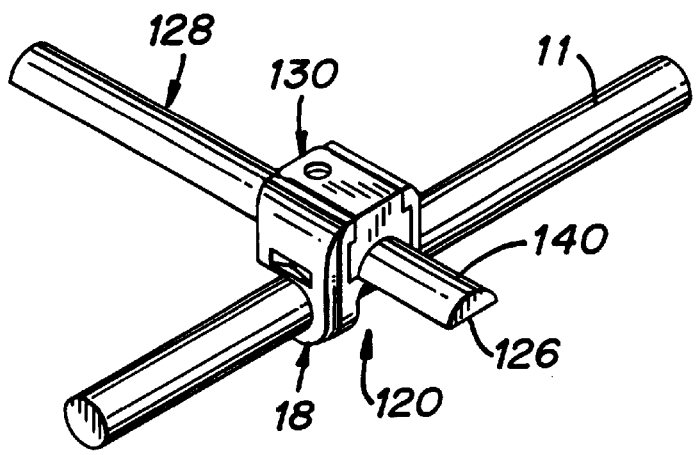
FIG. 16 is a perspective view of the assembled invention of FIG. 15.

The second side of the clip body 12 can include, but is not limited to, a short hemi-cylinder rod (Clip 10A, FIG. 2), a laterally extending hemi-cylinder rod with a plurality of vertical teeth (Clip 10B, FIGS. 3–4), a second pair of mirror image hemi-cylindrical shells (Clip 10C, FIGS. 8–9), a laterally extending rod tapering from a proximal cylindrical shape to a distal hemi-cylinder shape (Clip 10D, FIG. 12), or an outwardly extending U-shaped receptacle designed to receive a semi-cylindrical or cylindrical rod and a locking cap device (Clip 10E, FIGS. 15–16). Each of these embodiments will be described below.

One embodiment of the transverse connector clip 10A is shown in FIG. 2. Here, the clip body 12 consists of a first side 14 as previously described (FIG. 1) and a second side 16 that comprises a preferably short laterally extending hemi-cylinder rod 40, however, any shaped rod could be utilized. The short hemi-cylinder rod 40 integral to the second side 16 of clip body 12 is shaped to facilitate installation of clip 10A by a user. A user can use the short rod 40 to manually engage and disengage the clip body 12 from a cylindrical rod 11 of two rods joined together in a spinal fixation system. Clip 10A can be used to connect transverse connector clips having laterally extending hemi-cylinder rods 10B (FIG. 6). One advantage of the inventive connector clip 10A over prior art connectors is that clip 10A is a single piece connector, thereby reducing the amount of assembly of the spinal fixation system required by prior art connectors during surgery.

Another embodiment of the present invention is the transverse connector clip 10B (FIG. 3). Here, the clip body 12 consists of a first side 14 as previously described (FIG. 1) and a second side 16 that includes a laterally extending hemi-cylinder rod 50 having a first side 52, a second side 54, and a longitudinal axis LA1—LA1. However, other shapes can be utilized for the laterally extending hemi-cylinder rod 50. The first side 52 contains a plurality of vertically placed teeth 56 extending along the longitudinal axis LA1—LA1. FIG. 4 shows a perspective view of the second side 54 of connector clip 10B.

Clip 10B is designed to be interlocked to a second clip 10B (FIG. 5). The first sides 52 of the hemi-cylinder rods 5 are connected to each other via the plurality of vertical teeth 56 extending along the longitudinal axes LA1—LA1 of the hemi-cylinder rods 50. The clips 10B can transversely connect two longitudinal rods 11 placed at varying distances from each other with the plurality of teeth 56 accommodating the variable distance. This variable distance is indicated by the lateral motion arrows LM1—LM1 (FIG. 5). This ability of the clips 10B provides a significant advantage during surgery where many such adjustments are necessary to fine tune the alignment of the assembly in the patient.

The connection between clips 10B can be maintained by using transverse connector clip 10A (FIG. 6). When the first sides 52 of the hemi-cylinder rods 50 are engaged by the interlocking of the plurality of vertical teeth 56, the second sides 54 form a cylindrical rod having a diameter that is slightly larger than the inner diameter 22 defined by the inner surface 24 of the hemi-cylindrical shells 18 and 20 of clip 10A. Thus, the hemi-cylindrical shells 18 and 20 of clip 10A can snap onto the connected hemi-cylinder rods 50 of clips 10B as if the connected hemi-cylinder rods 50 were a single cylindrical rod 11.

While FIG. 6 illustrates a transverse connector clip 10A of the present invention connecting the laterally extended hemi-cylinder rods 50 of clips 10B, it should be understood that any connecting device known to one skilled in the art can be used to connected the hemi-cylinder rods 50. The advantage of using the transverse connector clip 10A of the present invention, however, is that it consists of a single piece which facilitates surgery by reducing the number of pieces that need to be assembled.

The spinal rod assembly using transverse connector clips 10A and 10B of the present invention connects to longitudinal rods 11 that are connected to a human vertebrae 91 as schematically shown in FIG. 7. Two cylindrical rods 11 are each connected to a transverse connector clip 10B through the mirror image hemi-cylindrical shells 18 and 20. The laterally extending hemi-cylinder rods 50 of clips 10B are connected to each other by the interlocking of the plurality of vertical teeth 56. This connection is maintained by clip 10A.

Clip 10C (FIGS. 8–9) is an alternate embodiment of the transverse clip connector 10 having a clip body 12 with a first side 14 and a second side 16. The first side 14 is as previously described (FIG. 1). The second side 16 of the clip body 12 comprises a second set of mirror image hemi-cylindrical shells 60 and 62. Like the hemi-cylindrical shells 18 and 20 on the first side 14 of clip body 12, hemi-cylindrical shells 60 and 62 can be placed on the second side 16 of the clip body 12 as shown (FIG. 8) or in mirror image relationship (not shown).

The second set of hemi-cylindrical shells 60 and 62 have an outer surface 64 and an inner surface 68. The inner surface 68 defines a rod bore 70 through which a cylindrical rod 88 can extend. Rod bore 70 has a diameter 72 that is slightly smaller than the diameter of the rod 88 it is designed to receive.

Clip 10C is designed to simultaneously connect two longitudinal rods 11 and a transverse rod 88 together. The cylindrical rods 11 connect to the first side 14 of the clip body 12 as previously described. Cylindrical rod 88 connects to the second side 16 of clip body 12 in a similar fashion. Namely, clip body 12 is placed on a cylindrical rod 88 at 90 degrees and turned so that the hemi-cylindrical shells 60 and 62 spread around the rod 88. The deflection of the hemi-cylindrical shells 60 and 62 and the inner diameter 72 allow the clip body 12 of clip 10C to securely clamp on the rod 88.

One advantage of having the second side 16 of the inventive clip body 12 comprising a second pair of hemi-cylindrical shells 60 and 62 is that it allows attachment of this second pair of shells 60 and 62 to various other rod types used in spinal surgery such as T-bar 80 (FIG. 10) and an I-bar (not shown). A T-bar 80 and an I-bar can horizontally bridge a pair of cylindrical rods 11 (FIG. 11) significantly strengthening the spinal fixation system.

T-bars 80 have a longitudinal body 82, a first end 84 and a second end 86. The first end 84 of T-bar body 82 has a cylindrical-shaped bar 88 perpendicularly connected to the T-bar body 82 (FIG. 10). This bar 88 can be connected to the second pair of hemi-cylindrical shells 60 and 62 of invention clip 10C as described above.

Two inventive clips 10C can be used to connect two cylindrical rods 11 via two T-bars 80 (FIG. 11). In this example, two clips 10C are each connected to bars 88 on the first ends 84 of two separate T-bars bodies 82. The second ends 86 of each T-bar body 82 is then connected to each other via a tapered locking sleeve 90 or by any means known to those of skill in the art. The relative placement of one cylindrical rod 11 to the other can be adjusted by adjusting the T-bar connection as indicated by circular motion arrows CM1—CM1 and CM2—CM2. In this way, the inventive clips 10C can facilitate the creating of the desired transverse bridge between two cylindrical rods 11 using a minimum number of pieces.

While the embodiment shown here (FIG. 11) shows invention clips 10C connected to two different T-bars 80, it should be understood that two clips 10C can also be connected to the opposite ends of a single I-bar (not shown). An I-bar has a longitudinal body and a first and second end. The first end has a first rod-shaped bar positioned perpendicular to the I-bar body. The second end has a second cylindrical-shaped bar positioned perpendicular to the I-bar body. The first pair of hemi-cylindrical shells 18 and 20 of clip 10C is connected to a first cylindrical rod 11 while the second pair of hemi-cylindrical shells 60 and 62 is connected to the first bar on the first end of the I-bar body. A second invention clip 10C is connected to a second cylindrical rod 11 through hemi-cylindrical shells 18 and 20 and then to the second bar on the second end of the I-bar body via hemi-cylindrical shells 60 and 62. In this way, the I-bar provides a horizontal bridge between two cylindrical rods by connection via the invention clips 10C.

In another embodiment of the inventive clip 10, the first side of the clip body 12 is as previously described, while the second side of the clip body 12 comprises a laterally extending rod 100 having a first side 102, a second side 104, a longitudinal axis LA1—LA1, and a proximal 106 and distal 108 end (Clip 10D, FIG. 12). The proximal end 106 is cylindrical in shape and tapers to a hemi-cylindrical shape at the distal end 108.

Clip 10D is designed to connect to another clip 10D (FIGS. 12–14) via the laterally extending tapering rods 100. The laterally extending tapered rods 100 are connected to each other by mating the first sides 102 together. This connection can be maintained with any of the devices known to those of skill in the art including, but not limited to, a tapered locking sleeve 90. This tapered locking sleeve 90 consists of an inner 92 and outer 94 sleeve portion. Inner sleeve portion 92 has an inner surface 96 and outer surface 98; and outer sleeve portion 94 has an inner surface 110 and outer surface 112. The outer surface 98 of the inner portion 92 has a diameter 114 slightly smaller than a diameter 116 of the inner surface 110 of the outer sleeve 94 so as to allow the inner sleeve portion 92 to be placed concentrically inside the outer sleeve 94 in order to lock the inner sleeve portion 92 and outer sleeve portion 94 together.

To assemble clips 10D, the outer sleeve portion 94 is positioned on a laterally extending hemi-cylinder bar 100 of a first connector clip 10D and the inner sleeve portion 92 is positioned on a laterally extending hemi-cylinder bar 100 of a second connector clip 10D (FIGS. 12–14). The first sides 102 of the laterally extending hemi-cylinder bars 100 of the first and second clips 10D are mated and held in locking engagement by the tapered sleeve 90.

The distance between the two connector clips 10D can be laterally adjusted by moving the laterally extending tapered rods 100 as indicated by the arrows LM2—LM2 in FIG. 13. When the first sides 14 of each clip body 12 of clips 10D are connected to two different cylindrical rods 11 via the hemi-cylindrical shells 18 and 20 on the first side 14 of the clip body 12 (FIG. 14), lateral adjustment of the tapered rods 100 laterally adjusts the relative position of the cylindrical rods 11 to which the connector clips 10D are connected. This provides the user with some flexibility in adjusting the alignment of the cylindrical rods 11 in a spinal fixation apparatus during surgery.

A spinal rod assembly using connector clips 10D and a tapered locking sleeve 90 connects to longitudinal rods 11 that are connected to a human vertebrae 91 as schematically shown in FIG. 14. Two cylindrical rods 11 are each connected to a clip 10D through the mirror image hemi-cylindrical shells 18 and 20. The laterally extending tapered bars 100 of clips 10D are held together with a tapered locking sleeve 90. The assembly of the tapered locking sleeve 90 is also shown.

Several means of clamping the various types of laterally extending rods from the second side 16 of the invention clip body 12 have been described above including another transverse clip of the present inventive clip 10A (FIG. 6) and a tapered sleeve 90 (FIGS. 12–14). However, it should be understood that laterally extending hemi-cylinder rods can be connected by any other connecting means known to one skilled in the art.

In yet another embodiment of the inventive transverse connector clip 10, the first side 14 of the clip body 12 is as previously described, while the second side 16 of the clip body 12 comprises an outwardly extending rod holding portion 120 and a locking mechanism 130. The rod holding portion has a longitudinal axis positioned perpendicular to the longitudinal axis LA1—LA1 of the first side 14 of the clip body 12. The locking mechanism 130 is configured to engage with the rod holding portion 120 in order to locking the longitudinal rod into the rod holding portion 120. The rod holding portion can be in the shape of a solid holding portion having a through bore for receiving a hemi-cylindrical or cylindrical rod and the locking mechanism can be of any locking mechanism known to one skilled in the art, such as tapered locking caps, set screws or locking nuts. In one embodiment, the holding portion is a U-shaped holding portion 120 having a longitudinal axis LA3—LA3 positioned perpendicular to the longitudinal axis LA1—LA1 of the first side 14 of connector clip 10E (FIGS. 14–15). The U-shaped holding portion 120 has an upper portion 122 and a lower portion 124. The lower portion 124 is substantially planar and is configured to receive a flat side 126 of a hemi-cylindrical rod 128. Alternatively (not shown), the lower portion 124 of the U-shaped portion 120 can be configured to receive a cylindrical rod 11. A locking mechanism for the U-shaped portion 120 can include a locking cap 130 with an upper 132 and lower side 134 configured to slide into and mate with the upper portion 122 of U-shaped portion 120. Upper side 132 of locking cap 130 has a tapered portion 136 that engages and mates with a tapered portion 138 in the upper portion 122 of the U-shaped portion 120. The lower side 134 of the locking cap 130 is configured to accommodate an arcuate side 140 of the hemi-cylindrical rod 128.

The advantage of the inventive clip 10E, when used in combination with the locking cap 130, the hemi-cylinder support bar 128, and cylindrical rod 11 (FIGS. 15–16) is that connecting clip 10E is a single piece that connects two rods together, thus reducing the requirement of the prior art connectors to assemble small pieces of hardware during the surgical procedure.

It should be understood that in keeping with spinal surgery techniques, a plurality of cylindrical rods 11 can be used, each with a plurality of attachment devices affixed thereto, with the present attachment devices transversely connecting either two rods 11 together or connecting portions of rods together in other alignments.

The foregoing disclosure and description of the invention are illustrative and explanatory thereof, and various changes in the details of the illustrated apparatus and construction and method of operation may be made without departing from the spirit of the invention.

What is claimed is:

1. A spinal fixation system comprising:
    a) a first clip body having a pair of opposed spaced apart arcuate rod engaging hooks for engaging a first elongated spinal rod and a laterally extending transverse connector;
    b) a second clip body having a pair of opposed spaced apart arcuate rod engaging hooks for engaging a second elongated spinal rod and a laterally extending transverse connector; and
    c) a fastener for securing the transverse connector of the first clip body and the transverse connector of the second clip body to one another, the fastener having an inner portion with an outer surface and an outer portion with an inner surface, the inner surface of the outer portion being adapted and configured to slidably engage the outer surface of the inner portion to radially compress the inner portion.

2. A spinal fixation system as recited in claim 1, wherein the transverse connector extending from the first clip body and the transverse connector extending from the second clip body have complementary cross-sectional configurations such that together the pair of transverse connectors define a circular cross-section.

3. A spinal fixation system as recited in claim 2, wherein the fastener is defined at least in part by a cylindrical compression sleeve, the inner surface of which is configured to engage the outer surface of the inner portion of the fastener.

4. A spinal fixation system as recited in claim 2, wherein the transverse connector extending from the first clip body and the transverse connector extending from the second clip body have complementary mating surfaces.

5. A spinal fixation system as recited in claim 4, wherein the complementary mating surfaces are substantially planar.

6. A spinal fixation system as recited in claim 1, wherein each transverse connector is formed integral with the clip body with which it is associated.

7. A spinal fixation system comprising:
    a) a first body portion having a rod clamp for engaging a first elongated spinal rod and a transverse connector;
    b) a second body portion having a rod clamp for engaging a second elongated spinal rod and a transverse connector; and
    c) a fastener for securing the transverse connector of the first body portion and the transverse connector of the second body portion to one another, the fastener having an inner portion with an outer surface and an outer portion with an inner surface, the inner surface of the outer portion being adapted and configured to slidably engage the outer surface of the inner portion to radially compress the inner portion.

8. A spinal fixation system as recited in claim 7, wherein the transverse connector extending from the first clip body and the transverse connector extending from the second clip body are configured to mate with one another.

9. A spinal fixation system as recited in claim 8, wherein the fastener is defined at least in part by a cylindrical compression sleeve, the inner surface of which is configured to engage the outer surface of the inner portion of the fastener.

10. A spinal fixation system as recited in claim 7, wherein each transverse connector is formed integral with the body portion with which it is associated.

11. An apparatus for connecting spinal rods comprising:
    a) a first body member having first and second portions, the first portion defining a rod clamp for engaging a first spinal rod, the second portion defining a first elongated shaft section;
    b) a second body member having first and second portions, the first portion defining a rod clamp for engaging a second spinal rod, the second portion defining a second elongated shaft section configured to engage with the first elongated shaft section; and
    c) a locking sleeve adapted and configured to surround the first and second elongated shaft sections and secure the first and second elongated shaft sections together in an engaged condition by radial compression, the locking sleeve including an inner sleeve portion and an outer sleeve portion, the inner sleeve portion having an outer surface and the outer sleeve portion having an inner surface, the inner surface of the outer sleeve portion being adapted and configured to slidably engage the outer surface of the inner sleeve portion to radially compress the inner sleeve portion.

12. An apparatus as recited in claim 11, wherein the first elongated shaft section extending from the first body member and the second elongated shaft section extending from the second body member are adapted and configured to mate with one another.

13. An apparatus as recited in claim 11, wherein each shaft section is formed integral with the body member with which it is associated.

* * * * *